(12) United States Patent
Skidmore (10) Patent No.: US 9,396,533 B2
(45) Date of Patent: Jul. 19, 2016

(54) METHOD, SYSTEMS AND COMPUTER PROGRAM PRODUCTS FOR MEDICAL BRAIN IMAGING ANALYSIS

(76) Inventor: Frank M. Skidmore, Mountain Brook, AL (US)

(*) Notice: Subject to any disclaimer, the term of this patent is extended or adjusted under 35 U.S.C. 154(b) by 114 days.

(21) Appl. No.: 14/116,902

(22) PCT Filed: May 11, 2012

(86) PCT No.: PCT/US2012/037591
§ 371 (c)(1),
(2), (4) Date: Jan. 23, 2014

(87) PCT Pub. No.: WO2012/155077
PCT Pub. Date: Nov. 15, 2012

(65) Prior Publication Data
US 2014/0226888 A1  Aug. 14, 2014

Related U.S. Application Data

(60) Provisional application No. 61/484,889, filed on May 11, 2011.

(51) Int. Cl.
*G06T 7/00* (2006.01)
*A61B 5/00* (2006.01)
*G06K 9/62* (2006.01)
*A61B 5/055* (2006.01)

(52) U.S. Cl.
CPC ............ *G06T 7/0012* (2013.01); *A61B 5/4064* (2013.01); *G06K 9/6256* (2013.01);
(Continued)

(58) Field of Classification Search
CPC ... G06K 9/6256; G06K 9/626; G06K 9/6267; G06K 9/6277; G06K 2209/051; G06T 7/0012; G06T 7/0014; G06T 2207/20081; G06T 2207/30016; A61B 5/4064; A61B 5/4076; A61B 5/4082; A61B 5/4088; A61B 6/501; A61B 6/5211

See application file for complete search history.

(56) References Cited

U.S. PATENT DOCUMENTS

2005/0273007 A1  12/2005  Burbar ........................ 600/436
2006/0104494 A1   5/2006  Collins et al. ................ 382/128
(Continued)

FOREIGN PATENT DOCUMENTS

WO   WO 2009/146388 A1   12/2009   ............... A61B 5/05

OTHER PUBLICATIONS

International Search Report and Written Opinion for PCT/US2012//037591 mailed Jan. 7, 2013, 12 pages.

*Primary Examiner* — Andrew W Johns
(74) *Attorney, Agent, or Firm* — The Gache Law Firm, P.C.; Russell C. Gache (57) ABSTRACT

A method for analyzing brain images includes receiving a plurality of three-dimensional image datasets comprising a plurality of voxels for a corresponding plurality of subjects; dividing the plurality of three-dimensional image datasets into at least a first and a second group; dividing the first group into $A_1$ to $A_n$ subgroups; dividing the second group into $B_1$ to $B_n$ subgroups; determining statistical individual variability between datasets selected from the $A_1$ to $A_n$ subgroups and the $B_1$ to $B_n$ subgroups; determining statistical individual variability between datasets in the first and second groups responsive to the statistical individual variability between datasets selected from the plurality of three-dimensional image datasets in the $A_1$ to $A_n$ subgroups and the $B_1$ to $B_n$ subgroups; and for each of the first and second groups, generating a reliability map comprising a map of probabilities that a voxel in an image dataset of the respective first and second groups satisfies a predetermined statistical threshold.

25 Claims, 6 Drawing Sheets

(52) U.S. Cl.
CPC ............ *G06K9/6277* (2013.01); *G06T 7/0014*
(2013.01); *A61B 5/055* (2013.01); *A61B 5/4082*
(2013.01); *A61B 5/4088* (2013.01); *A61B
2576/026* (2013.01); *G06K 2209/05* (2013.01);
*G06T 2207/10072* (2013.01); *G06T 2207/20081*
(2013.01); *G06T 2207/30016* (2013.01)

(56) References Cited

U.S. PATENT DOCUMENTS

2008/0243395 A1   10/2008  Oosawa et al. ................. 702/19
2013/0195329 A1\*  8/2013  Canda ................. G06K 9/6267
                                                    382/128

\* cited by examiner

METHOD, SYSTEMS AND COMPUTER PROGRAM PRODUCTS FOR MEDICAL BRAIN IMAGING ANALYSIS

RELATED APPLICATIONS

This application is a 35 U.S.C. §371 national phase entry of PCT Application PCT/US2012/037591, filed May 11, 2012 and published in English on Nov. 15, 2012, as International Publication No. WO 2012/155077, and which claims the benefit under 35 U.S.C. §119(e) of U.S. Provisional Patent Application Ser. No. 61/484,889, filed May 11, 2011, the disclosure of each of which is incorporated herein by reference in its entirety.

FIELD OF THE INVENTION

The present invention relates to medical brain imaging.

BACKGROUND

Diagnosis and the identification of accurate biomarkers for diseases, including diseases of the human brain, are needed to improve early detection and prognosis. Imaging markers for neurodegenerative diseases have recently become clinically relevant. For example, "Pittsburgh compound B," a fluorescent analog of thioflavin, may be used in imaging beta amyloid plaques in Alzheimer disease (Klunk et al., "Imaging Brain Amyloid in Alzheimer's disease with Pittsburgh Compound-B," Ann. Neurol. 55: 306-19 (2004); Price et al., "Kinetic Modeling of Amyloid Binding in Humans using PET imaging and Pittsburgh Compound-B," J. Cereb. Blood Flow Metab. 25: 1528-47 (2005). An injection of Ioflupane $I^{123}$ with subsequent imaging using single positron emission tomography (SPECT), also known as DaTscan (Hauser R A, Grosset D G, [123I]FP-CIT (DaTscan) SPECT Brain Imaging in Patients with Suspected Parkinsonian Syndromes. J. Neuroimaging (2011)); XX:1-6), may be used to detect individuals with Parkinsonian disorders and is currently in clinical use to help differentiate causes of symptoms in individuals with suspected neurodegenerative Parkinsonism but equivocal clinical findings.

Both of these biomarkers use a known feature of a particular disorder, such as the deposition of a particular matrix of proteins (beta-amyloid plaques) or a regional reduction in binding of dopamine, to identify individuals with a particular disorder. Imaging biomarkers of this type generally use a specific property of an injected tracer to identify a subject with a particular disorder. These methods are by their nature limited to diagnosis or evaluation of a specific disorder in question and do not generally have broader applicability to answer other questions.

SUMMARY OF EMBODIMENTS OF THE INVENTION

In some embodiments, a method for generating a reliability map for analyzing brain images is provided. The method includes receiving a plurality of three-dimensional image datasets comprising a plurality of voxels for a corresponding plurality of subjects; dividing the plurality of three-dimensional image datasets into at least a first and a second group; further dividing the first group into $A_1$ to $A_n$ subgroups; further dividing the second group into $B_1$ to $B_n$ subgroups; determining statistical individual variability between datasets selected from the plurality of three-dimensional image datasets in the $A_1$ to $A_n$ subgroups and the $B_1$ to $B_n$ subgroups; determining statistical individual variability between the plurality of three-dimensional image datasets in the first and second groups responsive to the statistical individual variability between datasets selected from the plurality of three-dimensional image datasets in the $A_1$ to $A_n$ subgroups and the $B_1$ to $B_n$ subgroups; and for each of the first and second groups, generating a reliability map comprising a map of probabilities that a voxel in an image dataset of the respective first and second groups satisfies a predetermined statistical threshold.

In some embodiments, determining statistical individual variability between the plurality of three-dimensional image datasets in the first and second groups comprises combining a result of the statistical individual variability between datasets selected from the plurality of three-dimensional image datasets in the $A_1$ to $A_n$ subgroups and the $B_1$ to $B_n$ subgroups.

In some embodiments, a patient-specific three-dimensional image data set comprising a plurality of voxels for a patient is received, the patient-specific three-dimensional image data set is compared to the reliability maps of the first and second groups, and a likelihood that the patient-specific three-dimensional image data set is classified in the first group and/or the second group is determined.

In some embodiments, the first group comprises image datasets from a plurality of subjects having a known disease state and the second group comprises image datasets from a plurality of control subjects. The known disease state may include neurodegenerative disease. The known disease state may include Parkinson's disease. The known disease state may include one or more disease degrees and/or disease stages. The known disease state may include one or more subpopulations of a disease. The known disease state may include a risk of a degree of disease progression.

In some embodiments, statistical individual variability may be determined between datasets selected from the plurality of three-dimensional image datasets in the $A_1$ to $A_n$ subgroups and the $B_1$ to $B_n$ subgroups comprises generating a plurality of group variability maps. The plurality of group variability maps may include a statistical map generated from a bootstrapped or permutation analysis of the plurality of three-dimensional image datasets in the $A_1$ to $A_n$ subgroups and the $B_1$ to $B_n$ subgroups.

In some embodiments, a method of diagnosing a condition includes comparing a brain image for a subject with the reliability map determine a likelihood of a condition.

In some embodiments, a system for analyzing brain images includes a brain image database comprising a plurality of three-dimensional image datasets comprising a plurality of voxels for a corresponding plurality of subjects. An image analyzer module is configured to receive the plurality of three-dimensional image datasets comprising a plurality of voxels for a corresponding plurality of subjects, to divide the plurality of three-dimensional image datasets into at least a first and a second group, to further divide the first group into $A_1$ to $A_n$ subgroups, to further divide the second group into $B_1$ to $B_n$ subgroups, to determine statistical individual variability between datasets selected from the plurality of three-dimensional image datasets in the $A_1$ to $A_n$ subgroups and the $B_1$ to $B_n$ subgroups, to determine statistical individual variability between the plurality of three-dimensional image datasets in the first and second groups responsive to the statistical individual variability between datasets selected from the plurality of three-dimensional image datasets in the $A_1$ to $A_n$ subgroups and the $B_1$ to $B_n$ subgroups, and for each of the first and second groups, to generate a reliability map comprising a map of probabilities that a voxel satisfies a predetermined statistical threshold.

In some embodiments, a brain image reliability map as described herein is useful for analyzing brain images. The reliability map may be validated and may be is a diagnostic, predictive or prognostic map.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Embodiments according to the present invention may provide predictive image maps based on characteristics of physiologically derived imaging datasets. The term "medical image" as used herein refers to any suitable medical imaging technique that results in imaging datasets. Various types of medical imaging that may be used to create brain maps according to some embodiments include PET images, SPECT images, CT images and/or MRI or fMRI images. Imaging datasets may include three-dimensional datasets and/or datasets having additional dimensions of information, either with respect to adding a temporal dimension or with respect to adding an additional dimension of information regarding the contents of the three-dimensional dataset. For example, a typical MRI diffusion tensor map or fMRI dataset is a large, four-dimensional dataset, comprising multiple three-dimensional datasets. Each three-dimensional dataset within the sample may include several hundred thousand voxels of information relevant for generating MRI diffusion tensor maps. A six minute fMRI may include a plurality of three-dimensional images, with each image representing the state of a target organ with respect to the fMRI at a particular time point.

Embodiments according to the present invention may identify characteristics of a plurality of imaging datasets.

As used herein, "statistical individual variability" refers to a statistical measurement of variability on a voxel-by-voxel basis between images and/or a statistical measurement of variability of relationships between adjacent voxels between images. The images may be images from different subjects or the images may be from the same subject taken over time, e.g., before and after intervention and/or before and after a disease progression. A "probability map" or "reliability map" is used interchangeably and refers to a summated map of summated probabilities generated by a statistical analysis (e.g., bootstrapping or permutation analysis) of a plurality of images or relationships between images and/or relationships between regions in the images. A reliability map may be used to identify characteristics that can in turn be used to classify, diagnose and/or identify appropriate treatment for an individual or new subject using a brain image from the subject. A "voxel" is a volumetric pixel or volumetric picture element is a volume element, representing a value on a regular grid in three dimensional space.

Figure 1:
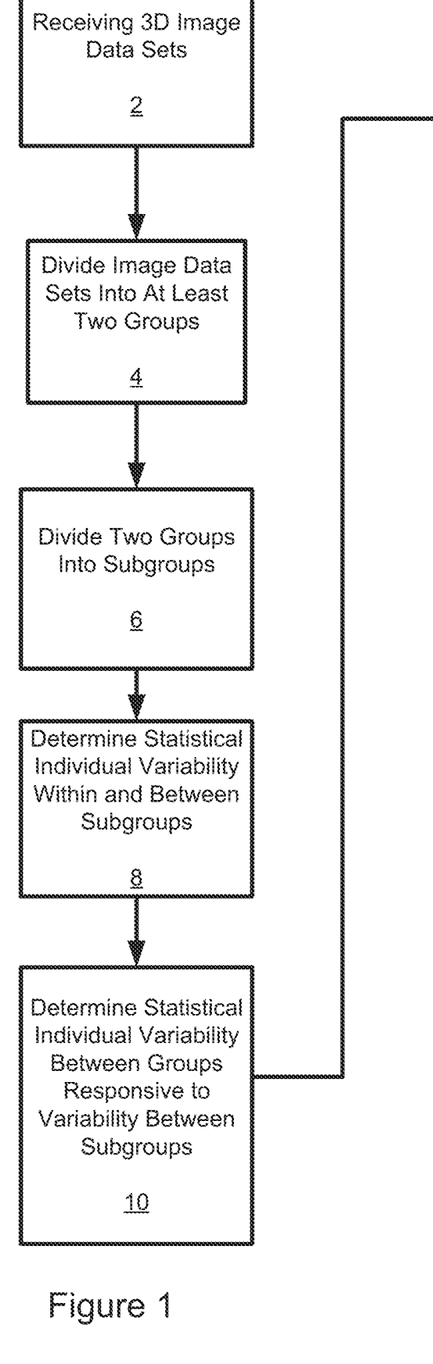
FIGS. 1-3 are flowcharts illustrating operations according to some embodiments.
Figure 2:
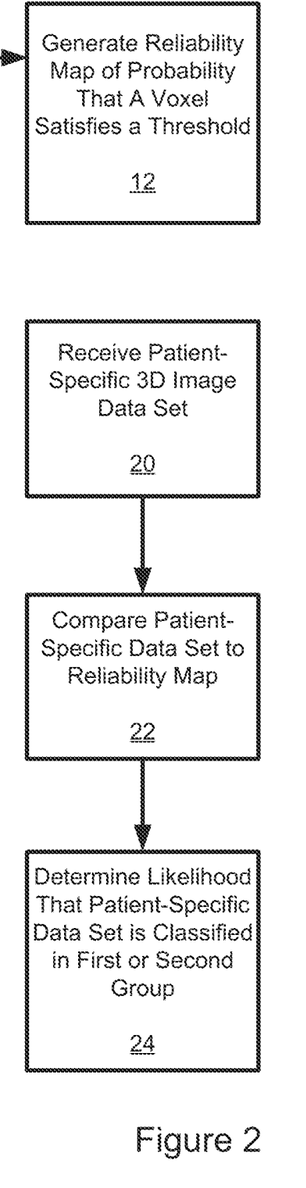
Figure 3:
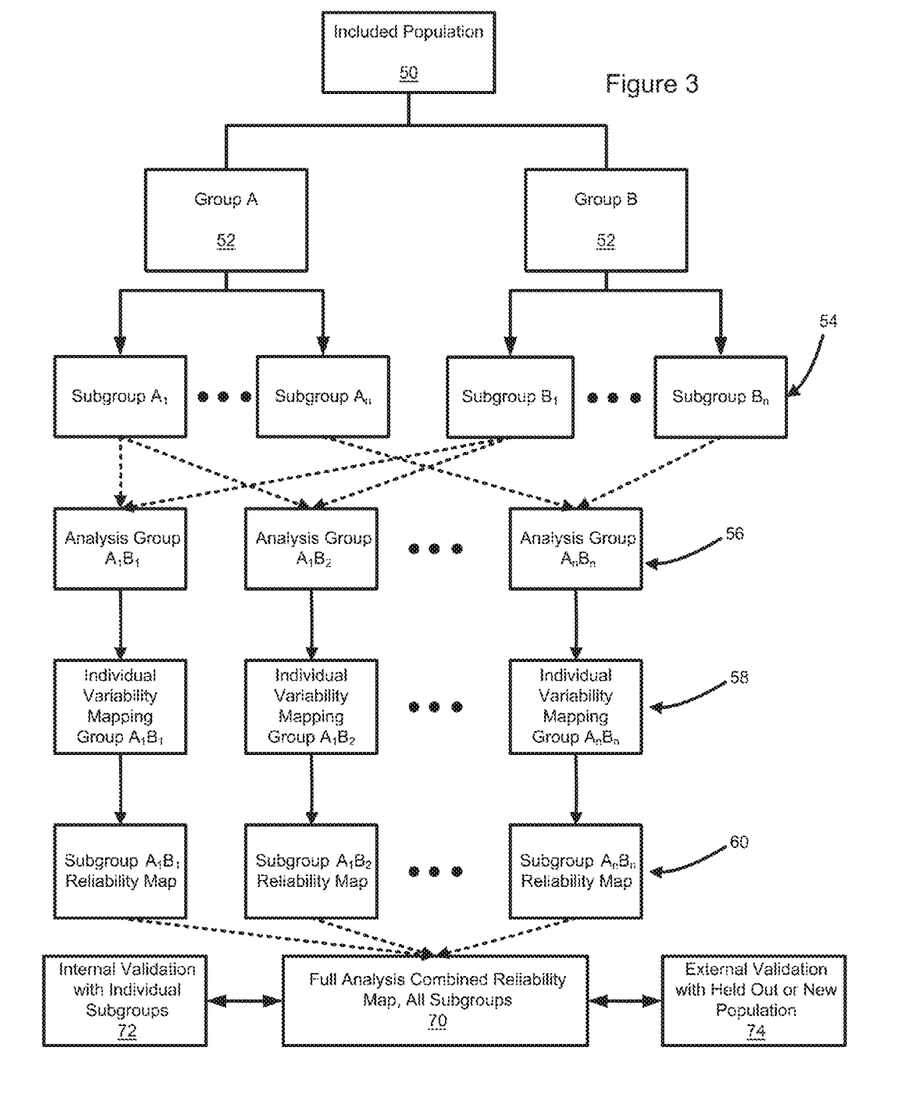

FIGS. 1-3 are a flowchart illustrating operations according to some embodiments. As illustrated in FIG. 1, a plurality of three-dimensional image datasets are received (Block 2). The datasets include a plurality of voxels for a corresponding plurality of subjects. The plurality of three-dimensional image datasets are divided into at least a first and a second group (Block 4). The first group is further divided into $A_1$ to $A_n$ subgroups, and the second group is further divided into $B_1$ to $B_n$ subgroups (Block 6). The statistical individual variability within and between between the plurality of three-dimensional image datasets in the $A_1$ to $A_n$ subgroups and the $B_1$ to $B_n$ subgroups is determined (Block 8). The statistical individual variability between the plurality of three-dimensional image datasets in the first and second groups is determined responsive to the statistical individual variability between the plurality of three-dimensional image datasets in the $A_1$ to $A_n$ subgroups and the $B_1$ to $B_n$ subgroups (Block 10). For each of the first and second groups, a reliability map comprising a map of probabilities that a voxel satisfies a predetermined statistical threshold is generated (Block 12).

In some embodiments as shown in FIG. 2, a patient-specific three-dimensional image data set comprising a plurality of voxels for a patient is received (Block 20). The patient-specific three-dimensional image data set is compared to the reliability maps of the first and second groups (Block 22). A likelihood that the patient-specific three-dimensional image data set is classified in the first group and/or the second group is determined (Block 24).

Embodiments according to the present invention that can rigorously analyze whether an image has the capacity to provide diagnostic, predictive, or prognostic information regarding a selected group will now be described. In the case of a positive assessment, some embodiments may be used to derive a predictive template or map. Predictive templates or maps may be used for a variety of purposes, including diagnosis, prognostic determination, or prediction (such as prediction of response to certain treatments or interventions) of multiple disorders, including diseases of the brain and spinal cord such as Alzheimer disease, Frontotemporal Dementia, Pick's disease, Parkinson disease, Progressive Supranuclear Palsy, Multiple Systems Atrophy, Amyotrophic Lateral Sclerosis, Autism, Schizophrenia, or other psychiatric or neurologic disorders. Detection of functional differences, such as disorders, in other human organ systems, when precision of localization of the organ system is possible to allow creation of overlying comparison maps, will also be possible using this method. Similarly, using this method for detection of functional differences, such as diseases and disorders, in non-human subjects, such as animals, would also be within the scope of the invention.

Without wishing to be bound by any particular theory, complex imaging datasets derived from clinical and/or animal populations, including human populations, may have characteristics driven by two levels of variability—individual variability, and group variability. Embodiments according to the present invention may allow evaluation and analysis of variability on the level of individual variability and group variability. An exemplary method is shown in FIG. 3. In this example, an included population (Block 50) of individuals is presented. Group A and group B (Block 52) are selected. Group A, for example, may represent individuals with a certain known disease or characteristic. Group B represents a second group of individuals (sometimes called a "control population") who do not have the characteristic of interest. It should be noted that this scenario is represented for the sake of example, and other types of division will occur to others skilled in the state of the art. In this representation, the goal of studying the included population (Block 50) is creating a predictive map that can predict group membership (A or B) in a Held Out or New Population 74. Within the Included Population (Block 50), the population is segregated into individuals in Group A and individuals in Group B. Each group is then further segregated into two or more subgroups (denoted in this example as Subgroup $A_1$ to Subgroup $A_n$ and Subgroup $B_1$ to Subgroup $B_n$) (Blocks 54). Characteristics of each Subgroup may include the following:

1) A given subgroup may be derived according to a predetermined known subgroup characteristic. For example, in the case of a disease or disorder, it is known that some individuals manifest a certain trait (such as cognitive decline or tremor), while others do not.

2) A given subgroup may be randomly determined. Randomly derived subgroups reflect the understanding, disclosed in this patent, that in complex imaging datasets there are similarities among subgroups of subjects either due to underlying relationships in the data that are unknown to the analyst, or due to random interactions within the dataset.

3) A series of subgroups may have members selected according to a method not related to a known subgroup or characteristic, or due to random assortment, but rather due to a method designed to optimally distribute subjects. Appropriate methods for assortment will occur to those skilled in the state of the art.

4) A given Subgroup may contain members that also exist in other Subgroups. For example, if a group of thirty individuals in a particular group were analyzed, the individuals may be segregated in three subgroups, each containing twenty subjects, in which each subgroup contains individuals that are also in at least one other subgroup.

Once analysis groups (Blocks 56) have been selected, the groups are compared. Turning to FIG. 3, in this case in this example subgroups from group B are compared with subgroups in group A. Created in this case are therefore analysis group $A_1B_1$ to $A_nB_n$ (Blocks 56). At this point, a statistical method for analysis of individual variability of data within the analysis group is used (Blocks 58). Multiple methods of permutation analysis are known to those skilled in the state of the art. In some embodiments, bootstrapping may be used as one method of representing individual variability within the selected analysis group. "Bootstrapping" refers to a class of statistical methods that use resampling to generate an empirical estimate of population distribution. In classical bootstrapping analysis, the assumption is made that the distribution of scores within a sample represents the distribution of scores within the general population (Bradley Efron and Robert Tibshirani. An introduction to the bootstrap. Monographs on statistics and applied probability; 57. Chapman and Hall, New York, 1993.). In this case, it is recognized that in large datasets, a higher level of complexity may occur within data such that, in some anatomic locations this assumption may be correct; however in other locations with the same dataset or image, random or nonrandom groupings (known or unknown to the analyst) may make this an inaccurate assumption. The bootstrapped results from a given analysis group (Blocks 56 and 58) may be taken as an estimate of population dynamics with respect to the group or measure.

With continued reference to FIG. 3, bootstrapping or permutation analyses generates a series of analysis group variability maps (Blocks 58). Each analysis group variability map represents a statistical map generated from a bootstrapped or permutation analysis. As a particular example of a specific embodiment of such a bootstrapped or permutation analysis, for example, twenty-five subjects might within a particular analysis be within each subgroup. For example, if subgroup $A_1$ and subgroup $B_1$ were selected, then the analysis group could therefore be analysis group $A_1B_1$. In a particular embodiment of the invention defined for the purposes of providing an example, a purely random process may be used to generate fifty analyzed subjects within a given iteration within each group, where subject may be either included, included more than once, or left out of the analysis at random. As a specific example, if group A had twenty-five subjects, $SA_1$ through $SA_{25}$, the following random subjects might be included from group A in a given analysis:

$SA_1$, $SA_1$, $SA_3$, $SA_3$, $SA_6$, $SA_8$, $SA_8$, $SA_9$, $SA_{10}$, $SA_{10}$, $SA_{11}$, $SA_{14}$, $SA_{15}$, $SA_{15}$, $SA_{16}$, $SA_{17}$, $SA_{18}$, $SA_{21}$, $SA_{22}$, $SA_{22}$, $SA_{22}$, $SA_{22}$, $SA_{23}$, $SA_{25}$, $SA_{25}$

Within group B, also including twenty-five subjects $SB_1$ through $SB_{25}$, if selected randomly the following subjects might be included:

$SB_2$, $SB_3$, $SB_4$, $SB_4$, $SB_4$, $SB_5$, $SB_5$, $SB_5$, $SB_8$, $SB_9$, $SB_9$, $SB_{11}$, $SB_{11}$, $SB_{14}$, $SB_{19}$, $SB_{19}$, $SB_{20}$, $SB_{21}$, $SB_{21}$, $SB_{21}$, $SB_{21}$, $SB_{22}$, $SB_{24}$, $SB_{24}$, $SB_{25}$

At this point it can be noted that in the analysis certain subjects are repeated one or more times, whereas other subjects are dropped from the analysis. We can note for example in Group A the following subjects are not included in the analysis:

$SA_2$, $SA_4$, $SA_5$, $SA_7$, $SA_{12}$, $SA_{13}$, $SA_{19}$, $SA_{20}$, $SA_{24}$.

Within Group B the following subjects are not included within the analysis:

$SA_1$, $SA_6$, $SA_7$, $SA_{10}$, $SA_{12}$, $SA_{13}$, $SA_{15}$, $SA_{16}$, $SA_{17}$, $SA_{18}$, $SA_{23}$

In cases in which bootstrapping is used as an analysis method, extraction of the identities of subjects who are not present within a specific analysis from the specific analysis can allow generation of data about individual subjects that can be used later for validation or other purposes. As shown in FIG. 3, some of these subjects may be used for the purposes of internal validation (Block 72). A number, $n_x$, of such maps may be created. In many cases, it is helpful to create a large number of statistical maps, such as 1,500 or more, while in certain cases (particular with large sample sizes), a much smaller number of maps may be possible. Once the statistical assessment is performed, information may be extracted from the statistical assessment. Multiple techniques of extracting information are possible and are well-known to those skilled in the state of the art.

In the exemplary analysis of FIG. 3 (and in our example later of a preferred embodiment of the invention), it is instructive to describe a method using thresholding. For example, a particular voxel-wise threshold of $p<0.05$ may be selected. Stated otherwise, within a given dataset, a threshold may be set such that it is assumed that 95% of the sample is below this statistical threshold, and 5% of the sample is above the threshold. The threshold may be applied to each of the maps such that voxels are described in a binary form, as either "0", or below threshold, or "1", above threshold. Within a given analysis involving a dataset with 100,000 voxels anatomically distributed throughout a three-dimensional structure, in which a certain measure is derived from calculations from a higher-dimensional dataset, it would be generally expected that roughly 5% of voxels within the sample would randomly be "above threshold" if a Gaussian distribution of values among the voxels is assumed (corresponding to 5,000 voxels). If $n_x=2,000$, then 2,000 maps are generated showing these results, among all the permutations developed during the group $A_1B_1$ individual variability mapping. Those skilled in the state of the art will recognize that, if these maps are summated, a construct is created, which can be represented as a purely mathematical spreadsheet, or as a three-dimensional visual map, that represents the estimate of the probability at a specific voxel that the lower limit of the confidence interval for the mean value of individuals in a particular subgroup is different from the mean value in this region for individuals in another particular subgroup. A representation of numerical probability of a particular statistical result in such a bootstrapped map, derived from a clinical sample including diseased and non-diseased subjects, is presented in FIG. 4.

Figure 4:
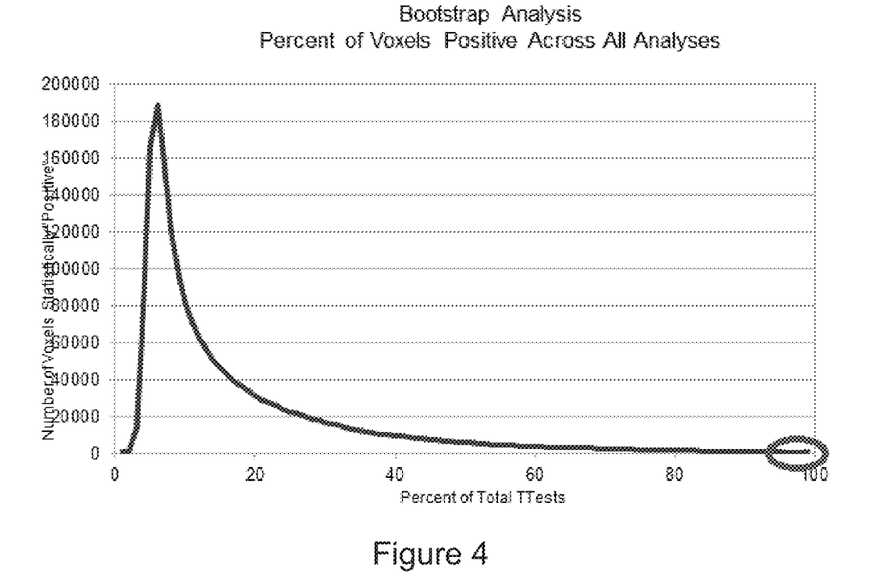
FIG. 4 is a graph illustrating a percentage of voxels that are positive for a plurality of analyses according to some embodiments.
Figure 5:
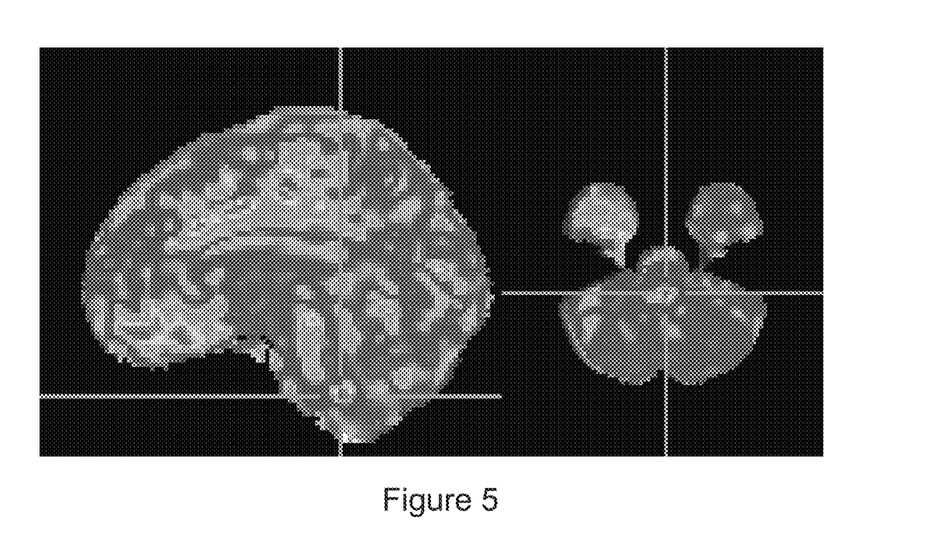
FIGS. 5-8 are brain images comprising a reliability map according to some embodiments.

As shown in FIG. 4, in this dataset, within a given voxel, there is a finite chance (peaking near 5%), that a given voxel will meet the selected statistical threshold among the analyses. The x-coordinate is represented as "percentage of total t-tests", but in the case of an analysis with a different focus, it could represent a different statistical test. In the represented sample, the 100% hash mark is reached at 2,000 analyses. We can see that among analyses, a progressively smaller proportion of the sample meets threshold. A two-dimensional slice from a three-dimensional map, derived from a similar clinical population, is shown in FIG. 5. In this map, which can be termed a "reliability map" or "variability map" with respect to the selected threshold, it can be noted that certain voxels, and associated regions, supercede the selected threshold in a large proportion of analyses (denoted in this case by warm colors and reds), whereas other voxels, and associated regions supercede the selected threshold in only a limited number of analyses (denoted by cool colors or blue-green colors).

Within a specific analysis group (Block 56), an analysis method may be applied. For example, a threshold may be selected without regard to cluster size (or any other parameters used in a standard model of analysis), representing the probability that a voxel in a repeated bootstrap analysis meets a given statistical threshold. Turning once again to FIG. 5, the following Table 1, generated from a real subject group, represents an example of a result of analysis. This table is generated roughly from the "tail" region of FIG. 4.

TABLE 1

Representative Result of a Bootstrap Analysis for $A_1B_1$

| % of Analyses Positive | 95 | 96 | 97 | 98 | 99 |
|---|---|---|---|---|---|
| Voxels | 3416 | 2649 | 1999 | 1337 | 757 |
| Fraction of Total Voxels | 0.00177994 | 0.0014 | 0.00104 | 0.000696655 | 0.00039444 |

Turning now to Table 1, 0.039444% of voxels, or 757 voxels met the threshold selected in 99 or more percent of analyses (corresponding a to score "above threshold" in 1980 or more consecutive analyses out of 2000). Lowering the threshold increases the number of voxels meeting threshold in iterative analyses, and in this case 0.17794% of voxels met the threshold in 95% or more of analyses (corresponding to a score "above threshold" in 1900 or more of the 2000 analyses). Individuals skilled in the art will recognize that this result corresponds to the lower limit of a confidence interval. Accordingly, within this particular analysis group A1B1, a map is generated such that, if the threshold of 97% of analyses positive or 1940 analyses is selected, the 1999 selected voxels show a difference of at least $p<0.05$ between all bootstrapped group analyses involving Subgroup $A_1$ and Subgroup $B_1$ in 97% of analyses, and further that these represent a level of stringency in selection such that only 0.104% of voxels within the sample met this criteria.

Figure 6:
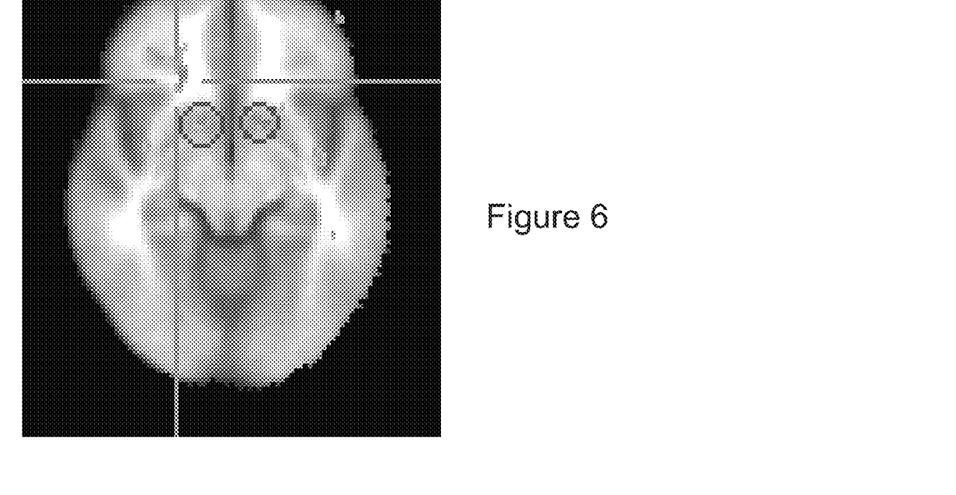

A map of potential use for prediction is therefore constructed. For example, using this map a series of anatomic regions may be selected including the voxels selected at a particular stringency, such as the largest 5 or 10 regions. As another example, a selection rule may be used, such as selecting the large 5 regions for example, and any contralateral region corresponding to the selected region when located in a mirrored location in the other hemisphere. FIG. 6 shows how this might be performed referring to a particular analysis. For example, the region encircled on the right is one of the larger regions of difference differing between the two populations among the repeated bootstrapped analyses. While the region encircled on the left is not among the largest regions, we note that this region is in a mirrored region on the opposite side of the brain, and it may be considered legitimate to in some cases generate a rule allowing inclusion of mirrored regions as "anatomically/functionally equivalent" when constructing a predictive template map.

Figure 7:
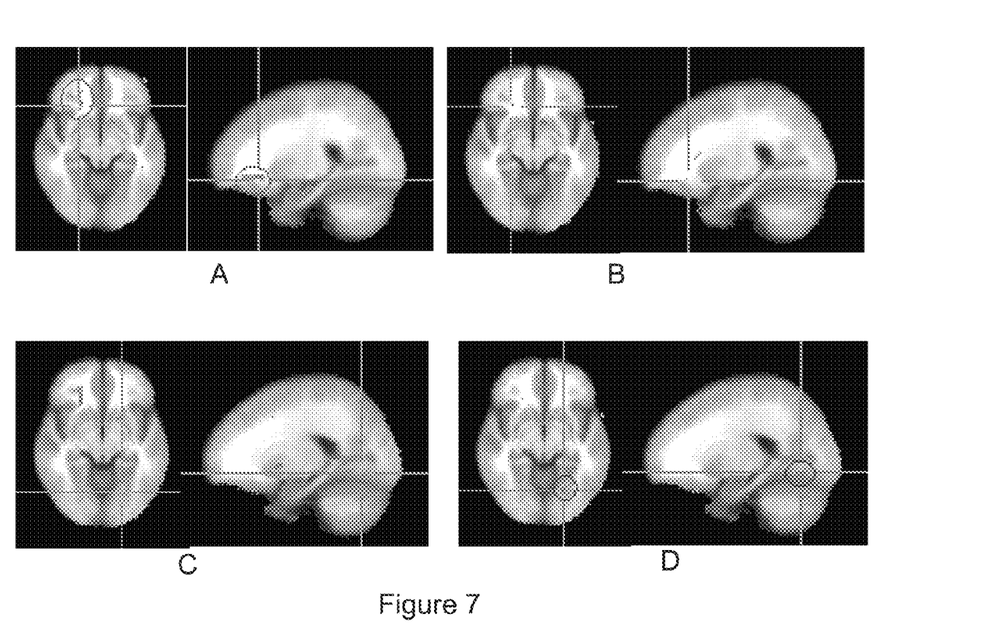

Emperically, it can be demonstrated at this point, given a sample of subjects, that by following this method that a solitary individual variability map (referred to for illustrative purposes as a full analysis subgroup reliability map $A_1B_1$ as an example of such a map) can have predictive utility. However, this map alone may also be improved to improve accounting for sample variability and maximize potential in a sample to generate a predictive map. As illustrated in FIG. 7, the results from two separate subgroup reliability maps selected from two groups from the same included population are shown. For illustrative purposes, two-dimensional slices drawn from a three-dimensional image are shown. On the left, results from the first subgroup analysis are shown. On the right, results from a second subgroup analysis are shown. In each case, some individuals from each subgroup are in both analyses, while some individuals within a given subgroup are in only one analysis. A moderate-sized region of difference (encircled in image A) that is present in the first full analysis subgroup reliability map, but is not in the second full analysis subgroup reliability map. Conversely, a moderate region (encircled in image B) that is present in the second full analysis subgroup reliability map, but is not in the first full analysis subgroup reliability map. In both cases, the regions in question were the largest regions within their respective analysis in terms of size and, if size were used as the sole arbiter, in each case these were the "most significant" region superseding the statistical threshold in use for this analysis. However, when these specific large regions are used as an assay for prediction, neither region is better than 50% (chance) in predicting group membership of a member of a "held out" or new population—nor given this finding on separate full analysis subgroup reliability maps would good prediction potential in these regions be expected.

Figure 8:
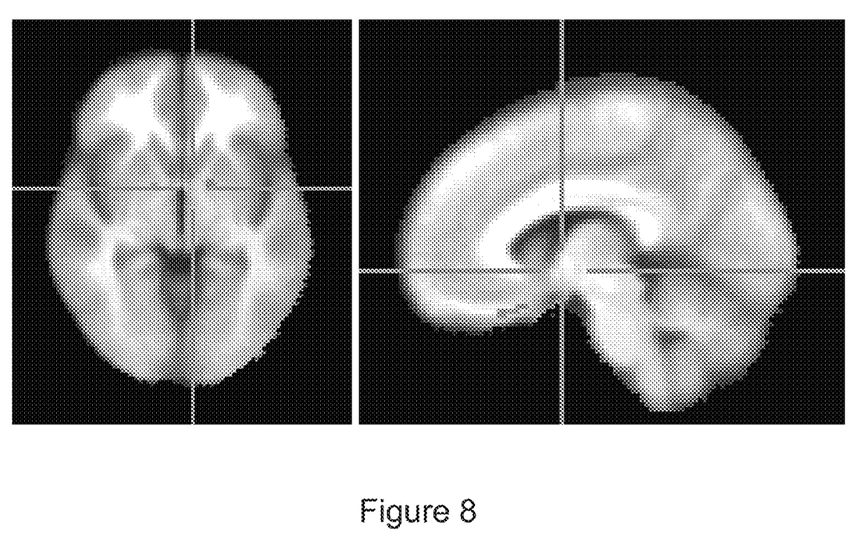

Accordingly, these regions diverging between analyses represent subgroup effects related to higher level complex relationships within an imaging dataset. Specifically, if 30 random healthy individuals with 500,000 bits of information regarding structure or function of the brain of each individual were selected, or 30 random individuals with a particular disease, it would be reasonable to surmise that there might be one or more regions among these individuals in which there is a powerful correlation either simply by chance, or due to some factor unknown to the analyst (for example, when a population of drug users signs up as control subjects, or with respect to a disease, a certain subgroup within a particular regional population has the disease due to a certain genetic cause that has an impact on the brain map, while others do not share this factor). The result of unknown or random factors creates findings on level of complexity above that of the individual subject. Specifically, it can be stated that a given statistical analysis is likely to pick up differences between samples related to actual differences, related to either random factors or unknown factors within the sample, between the subject groups that may have nothing to do with the specific question that is of interest. This may occur in both small and large datasets due to a complex interaction of individual and random associative group affects. A generated predictive map may therefore account for these random higher level subgroup effects. In FIG. 8, the first full analysis subgroup reliability map is combined with the second full analysis subgroup reliability map, to arrive at a combined reliability map in which both subgroups mitigate the individual subgroup findings. Enhanced in this analysis are the regions that are shared between the subgroup analyses, while factors present within only one subgroup analysis are muted. In general, a visible decrease in what appears to be "noisy" possible extraneous signal is also noted to be muted when we visually compare this analysis with the above subgroup analysis in FIG. 7.

Prediction:

Once a reliability map is created, various techniques may be utilized to use the map for predictive purposes. For example, in the case of a two group comparison, regional signal within a particular region of interest known to be predictive may be averaged among individuals with or without the disease in question. Results may be summated or averaged. Results above or below a predetermined threshold either with respect to specific regions or with respect to an average of more than one region may be used to classify subjects. Similarly, a principle component analysis may be generated within pre-selected regions, and this may be used to segregate subjects into discrete classes. Numerous other methods of developing a predictive template, once a reliability map is created according to the methods disclosed, will occur to those skilled in the state of the art.

Validation:

Once one or more subgroup reliability maps are created, the map can be validated via internal or external validation as illustrated in FIG. 3 (Blocks 72 and 74). Internal validation can use a "left-out" analysis. As will be noted above, within any given bootstrapped analysis one or more subjects will have been "left out" of the analysis. If these "left out" subjects are tracked, then results can be collated and a independently derived "left out" reliability map can be created for each subject using a combination of the appropriate analyses from one or more episodes of subgroup individual variability mapping. For example, returning to FIG. 3, it is assumed that an analysis is performed involving 2000 iterations each for Groups $A_1B_1$ to $A_nB_n$. Within each of these subgroup analyses, a certain number of analyses will have excluded a particular subject (e.g., $SA_1$). Depending on the randomization process, perhaps in some number of cases (in this example, 801 cases) in group $A_1B_1$, $SA_1$ was not included in the analysis. In Group $A_1B_2$, perhaps $SA_1$ was excluded in 911 analyses, and so on. If we collate all these results in some fashion to display a combined analysis of all subgroups, an estimate for the capacity of the mapping process to create a map that predicts a subject class of $SA_1$ may be created. This internal validation may be expressed as sensitivity and specificity of the analysis process for detecting presence or absence of the condition within the included population. An external validation is produced when the full analysis combined reliability maps for all subgroups are used to predict group membership of a "held out" or new population. Accordingly, rigorous, repeatable estimates of the capability of a given imaging method to produce a clinically relevant, predictive map may be achieved.

Alternative Mapping Goals:

Embodiments according to the present invention are described above with respect to segregating two groups, e.g., a control group and a group with a particular characteristic. However, it should be understood by those of skill in the art that other groupings may be used. For example, it may be a goal to associate a particular group with a particular parameter. In this case, it may be reasonable to use a regression model, or a multiple regression model, to generate a predictive template with respect to one or more regressors. If we are using a simple regression, a single Group is compared with one or more factors such as measure of disease severity, mood changes, or cognitive changes. A single bootstrapped analysis in some case might create a complex, and sufficient predictive map. However bootstrapping with multiple subgroups would create a more optimal prediction template that would be more rigorously resistant to individual subject and random group effects. As noted previously, principle component analysis might also be used either within regions defined by our methods, or as the bootstrapped statistical method to create mapped regions of analysis that might be useful for predictive purposes. The disclosed technique, within a given population, may provide an estimate of the relative capability of different four-dimensional imaging datasets to provide a useful clinical prediction; this technique can therefore assist in optimizing an entire field of inquiry for production of predictive maps. A variety of methods of assigning statistical qualities of various voxels may be generated, including assigning voxel relevancy on a variable or sliding basis with respect to relationship with the center of a particular region of interest considered potentially "predictive." Many additional complex statistical goals will occur to those skilled in the state of the art, and are within the scope of the invention. It should be understood that although embodiments are described with respect to MRI or fMRI scans, any suitable imaging method may be used to create a prediction based on a three-dimensional map derived from a series of calculations from a four-dimensional dataset. Multiple different calculations referring to different aspects of the four-dimensional dataspace might be included in a predictive template. Additionally, any additional imaging type may be used as an additional data dimension to be analyzed (e.g., imaging protocols such as structural, functional, diffusion tensor, or PET/SPECT imaging may be combined into specific, predictive templates may increase global prediction).

Embodiments according to the present invention may be used to generate diagnostic, predictive, and prognostic reliability maps based on imaging in human or animal subjects for clinical or research use. Moreover, a likelihood of a particular degree or stage of disease and/or a likelihood of disease progression may be estimated.

Example

Embodiments according to the present invention may not be described with respect to the following non-limiting example.

Twenty individuals with Parkinson disease and twenty-two healthy controls were enrolled into an imaging study including a Diffusion Tensor Image. In a first included population, seven healthy controls were held out of analysis. A repetitive bootstrapped process, as described above, was performed, to create a subgroup individual variability map. The top 0.5% of voxels were chosen to create a provisional predictive template map. Mirrored regions in the olfactory region, globus pallidus, nucleus accumbens, the cingulate, and a region in the posterior occipital region were selected based on region size and position to create a predictive template map. This provisional map was successful in predicting group membership in 6/7 left out control subjects. Subsequently, in a second included population, the seven healthy controls were replaced in the analysis and six individuals with Parkinson disease were held out of analysis. Once again, the top 0.5% of voxels were chosen to create a provisional predictive template map. Mirrored regions in the olfactory region, globus pallidus, nucleus accumbens, left orbitofrontal, and the cerebellum were selected based on region size and position to create a predictive template map. This provisional map was successful in predicting group membership in all six out of six "left out" Parkinson disease subjects. Subsequently, an internal validation was performed. In this internal validation, the bootstrapped statistical analyses in which each of the forty-two subjects was left out was correctly attributed to each individual left out subject. Predictive maps including mirrored regions in the olfactory cortex, globus pallidus, nucleus accumbens, and dorsal motor nucleus were selected based on size and statistical properties. It should be noted that the regions selected correlate well with regions that are affected over time in Parkinson disease according to standard pathological understanding of the disorder (Braak, et al., "Staging of Brain Pathology Related to Sporadic Parkinson's Disease," Neurobiol Aging; 24 (2)" 197-211 (2003)). However, it should also be noted that none of these regions has been generated previously as part of a predictive template using any currently utilized analysis technique. A predictive template was generated using the mean value within each cluster, and each cluster was averaged to create an average value among all clusters. Subjects were analyzed to determine if they fell either above or below this mean, which corresponded to diagnostic class. The predictive template was successful in identifying twenty out of twenty Parkinson disease subjects (Sensitivity 100%), and 21/22 control subjects (Specificity 95%).

For comparison, a standard analysis was performed. Using voxel-wise thresholding at $p<0.05$, and selecting up to 5 clusters within each analysis that were statistically significant at a cluster level of $p<0.01$, a predictive template was created. Predictive template was generated using the mean value within each cluster, and each cluster was averaged to create an average value among all clusters. Subjects were analyzed to determine if they fell either above or below this mean. "Significant" regions varied widely across analyses. A new predictive template was generally created therefore for each analysis due to inter-analysis variability. The predictive template at this significance level was successful in accurately identifying nine out of twenty PD subjects (sensitivity less than chance) and twelve out of twenty-two control subjects (specificity 55%). An identical analysis was performed using a voxel-wise thresholding at $p<0.01$, and selecting once again up to 5 clusters within each analysis that were statistically significant at a cluster level of $p<0.01$. In this analysis, Parkinson disease was correctly identified in twelve out of twenty cases (sensitivity 60%), and healthy controls were correctly identified in nine out of twenty-two cases (less than chance). Another identical analysis was performed using voxel-wise cluster thresholding at $p<0.001$, selecting all regions meeting this stringent threshold that were significant at a cluster level significance of $p<0.05$. In this analysis, Parkinson disease was correctly identified in eleven out of twenty cases (sensitivity 55%), and healthy controls were correctly identified in thirteen out of twenty-two cases (specificity 58%). Maps created using standard techniques did not in general correlate well with regions selected using the proposed method, nor were regions generated using standard statistical techniques closely aligned with regions that would be expected to be affected in Parkinson disease; rather, cortical regions not known to be specifically affected by the disorder were selected as "significant" using standard techniques of analysis.

In summary, using the methods described herein, initial bootstrapped analysis without combinatorial analysis of subgroups, accurately identified twelve out of thirteen subjects. With combined analysis, sensitivity and specificity were estimated using an internal validation method at very high (measured 100%) and 95% respectively. Using standard methods and the identical averaging algorithm, sensitivity and specificity of generated predictive templates approached chance, even when using the highest voxel-wise selection stringency.

This method therefore may generate robust statistical maps that are predictive in clinical populations and more clinically useful than maps generated using standard statistical techniques.

Figure 9:
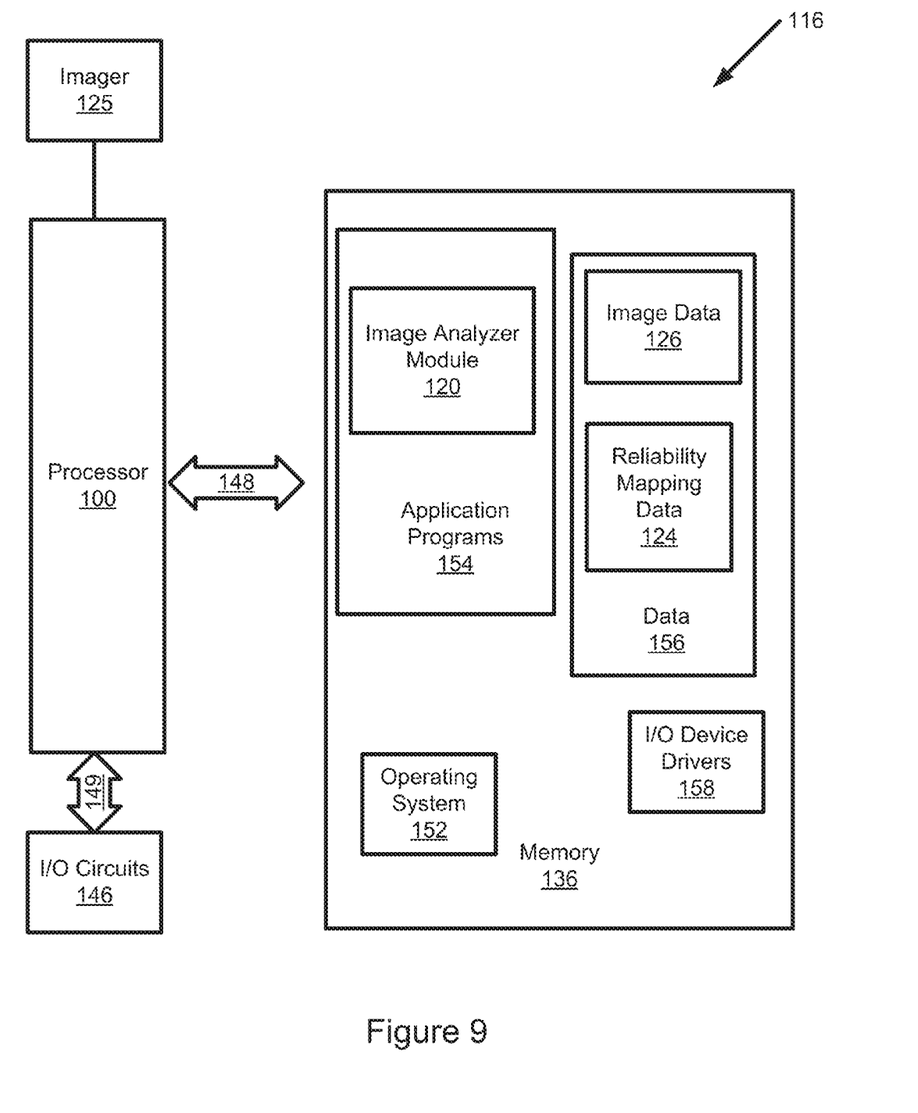
FIG. 9 is a block diagram illustrating systems, methods and computer program products according to some embodiments.

FIG. 9 illustrates an exemplary data processing system that may be included in devices operating in accordance with some embodiments of the present invention, e.g., to carry out the operations illustrated in FIG. 1-3. As illustrated in FIG. 9, a data processing system 116, which can be used to carry out or direct operations includes a processor 100, a memory 136 and input/output circuits 146. The data processing system 116 can be incorporated in a portable communication device and/or other components of a network, such as a server. The processor 100 communicates with the memory 136 via an address/data bus 148 and communicates with the input/output circuits 146 via an address/data bus 149. The input/output circuits 146 can be used to transfer information between the memory (memory and/or storage media) 136 and another component, such as an imager 125 (e.g., a medical imager) for imaging a subject. These components can be conventional components such as those used in many conventional data processing systems, which can be configured to operate as described herein.

In particular, the processor 100 can be a commercially available or custom microprocessor, microcontroller, digital signal processor or the like. The memory 136 can include any memory devices and/or storage media containing the software and data used to implement the functionality circuits or modules used in accordance with embodiments of the present invention. The memory 136 can include, but is not limited to, the following types of devices: cache, ROM, PROM, EPROM, EEPROM, flash memory, SRAM, DRAM and magnetic disk. In some embodiments of the present invention, the memory 136 can be a content addressable memory (CAM).

As further illustrated in FIG. 9, the memory (and/or storage media) 136 can include several categories of software and data used in the data processing system: an operating system 152; application programs 154; input/output device circuits 146; and data 156. As will be appreciated by those of skill in the art, the operating system 152 can be any operating system suitable for use with a data processing system, such as IBM®, OS/2®, AIX® or zOS® operating systems or Microsoft® Windows® operating systems Unix or Linux™. The input/output device circuits 146 typically include software routines accessed through the operating system 152 by the application program 154 to communicate with various devices. The application programs 154 are illustrative of the programs that implement the various features of the circuits and modules according to some embodiments of the present invention. Finally, the data 156 represents the static and dynamic data used by the application programs 154, the operating system 152 the input/output device circuits 146 and other software programs that can reside in the memory 136.

The data processing system 116 can include several modules, including an image analyzer module 120 and the like. The modules can be configured as a single module or additional modules otherwise configured to implement the operations described herein for analyzing the motility profile of a sample. The data 156 can include reliability mapping data 124 and/or image data 126, for example, that can be used by the image analyzer module 120 to detect and/or analyze an image or group of images as described herein.

While the present invention is illustrated with reference to the image analyzer module 120, the reliability mapping data 124, and the image data 126 in FIG. 9, as will be appreciated by those of skill in the art, other configurations fall within the scope of the present invention. For example, rather than being an application program 154, these circuits and modules can also be incorporated into the operating system 152 or other such logical division of the data processing system. Furthermore, while the image analyzer module 120 in FIG. 9 is illustrated in a single data processing system, as will be appreciated by those of skill in the art, such functionality can be distributed across one or more data processing systems. Thus, the present invention should not be construed as limited to the configurations illustrated in FIG. 9, but can be provided by other arrangements and/or divisions of functions between data processing systems. For example, although FIG. 9 is illustrated as having various circuits and modules, one or more of these circuits or modules can be combined, or separated further, without departing from the scope of the present invention. In some embodiments, the operating system 152, programs 154 and data 156 may be provided as an integrated part of the imager 125.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claim is:

1. A method for generating a reliability map for analyzing brain images, the method comprising:
   a. receiving a plurality of three-dimensional image datasets comprising a plurality of voxels for a corresponding plurality of subjects;
   b. dividing the plurality of three-dimensional image datasets into at least a first and a second group;
   c. further dividing the first group into $A_1$ to $A_n$ subgroups;
   d. further dividing the second group into $B_1$ to $B_n$ subgroups;
   e. determining statistical individual variability between datasets selected from the plurality of three-dimensional image datasets in the $A_1$ to $A_n$ subgroups and the $B_1$ to $B_n$ subgroups;
   f. determining statistical individual variability between the plurality of three-dimensional image datasets in the first and second groups responsive to the statistical individual variability between datasets selected from the plurality of three-dimensional image datasets in the $A_1$ to $A_n$ subgroups and the $B_1$ to $B_n$ subgroups; and
   g. for each of the first and second groups, generating a reliability map comprising a map of probabilities that a voxel in an image dataset of the respective first and second groups satisfies a predetermined statistical threshold to thereby analyze brain images.

2. The method of claim 1, wherein determining statistical individual variability between the plurality of three-dimensional image datasets in the first and second groups comprises combining a result of the statistical individual variability between datasets selected from the plurality of three-dimensional image datasets in the A1 to An subgroups and the B1 to Bn subgroups.

3. The method of claim 1, further comprising:
   a. receiving a patient-specific three-dimensional image data set comprising a plurality of voxels for a patient;
   b. comparing the patient-specific three-dimensional image data set to the reliability maps of the first and second groups; and
   c. determining a likelihood that the patient-specific three-dimensional image data set is classified in the first group and/or the second group.

4. The method claim 1, wherein the first group comprises image datasets from a plurality of subjects having a known disease state and the second group comprises image datasets from a plurality of control subjects.

5. The method of claim 4, wherein the known disease state comprises neurodegenerative disease.

6. The method of claim 5, wherein the known disease state comprises Parkinson's disease.

7. The method of claim 4, wherein the known disease state comprises one or more disease degrees and/or disease stages.

8. The method of claim 4, wherein the known disease state comprises one or more subpopulations of a disease.

9. The method of claim 4, wherein the known disease state comprises a risk of a degree of disease progression.

10. The method of claim 1, wherein determining statistical individual variability between datasets selected from the plurality of three-dimensional image datasets in the $A_1$ to $A_n$ subgroups and the $B_1$ to $B_n$ subgroups comprises generating a plurality of group variability maps.

11. The method of claim 10, wherein the plurality of group variability maps comprises a statistical map generated from a bootstrapped or permutation analysis of the plurality of three-dimensional image datasets in the $A_1$ to $A_n$ subgroups and the $B_1$ to $B_n$ subgroups.

12. A method of diagnosing a condition as recited in claim 1, further comprising the step of analyzing a brain image for a subject based upon the generated reliability map to estimate a likelihood of a condition.

13. The method of claim 12, wherein the estimate of a likelihood of a condition comprises an estimated prognosis for developing the condition and the method further comprises comparing a brain image for a subject with the reliability map to determine a degree of risk for developing the condition.

14. The method of claim 12, wherein the estimate of a likelihood of a condition comprises an estimated prognosis of a subcondition within the condition and the method further comprises comparing a brain image for a subject with the reliability map to determine a likelihood of the subcondition.

15. The method of claim 14, wherein the subcondition comprises a likelihood of progression of symptoms and/or a development of additional symptoms.

16. The method of claim 12, the method further comprising comparing a brain image for a subject with the reliability map to determine a likelihood of a response to therapy.

17. A system for classifying brain images, the system comprising:
   a. a brain image database comprising a plurality of three-dimensional image datasets comprising a plurality of voxels for a corresponding plurality of subjects; and
   b. an image analyzer module configured to receive the plurality of three-dimensional image datasets comprising a plurality of voxels for a corresponding plurality of subjects, to divide the plurality of three-dimensional image datasets into at least a first and a second group, to further divide the first group into A1 to An subgroups, to further divide the second group into B1 to Bn subgroups, to determine statistical individual variability between datasets selected from the plurality of three-dimensional image datasets in the A1 to An subgroups and the B1 to Bn subgroups, to determine statistical individual variability between the plurality of three-dimensional image datasets in the first and second groups responsive to the statistical individual variability between datasets selected from the plurality of three-dimensional image datasets in the A1 to An subgroups and the B1 to Bn subgroups, and for each of the first and second groups, to generate a reliability map comprising a map of probabilities that a voxel satisfies a predetermined statistical threshold.

18. The system of claim 17, wherein the image analyzer module is configured to determine statistical individual variability between the plurality of three-dimensional image datasets in the first and second groups by combining a result of the statistical individual variability between datasets selected from the plurality of three-dimensional image datasets in the A1 to An subgroups and the B1 to Bn subgroups.

19. The system of claim 17, wherein the image analyzer module is configured to receive a patient-specific three-dimensional image data set comprising a plurality of voxels for a patient, to compare the patient-specific three-dimensional image data set to the reliability maps of the first and second groups, and to determine a likelihood that the patient-specific three-dimensional image data set is classified in the first group and/or the second group.

20. The system of claim 17, wherein the first group comprises image datasets from a plurality of subjects having a known disease state and the second group comprises image datasets from a plurality of control subjects.

21. The system of claim 20, wherein the known disease state comprises neurodegenerative disease.

22. The system of claim 17, wherein the image analyzer module is configured to determine statistical individual variability between datasets selected from the plurality of three-dimensional image datasets in the $A_1$ to $A_n$ subgroups and the $B_1$ to $B_n$ subgroups by generating a plurality of group variability maps.

23. The system of claim 22, wherein the plurality of group variability maps comprises a statistical map generated from a bootstrapped or permutation analysis of the plurality of three-dimensional image datasets in the A1 to An subgroups and the B1 to Bn subgroups.

24. The system as recited in claim 17, wherein said system is utilized as a diagnostic map for patient evaluation.

25. A computer program product for generating a reliability map for analyzing brain images, the computer program product comprising:
  a. a non-transitory computer readable storage medium having computer readable program code embodied in said medium, the computer readable program code comprising:
    i. computer readable program code configured to receive a plurality of three-dimensional image datasets comprising a plurality of voxels for a corresponding plurality of subjects;
    ii. computer readable program code configured to divide the plurality of three-dimensional image datasets into at least a first and a second group;
    iii. computer readable program code configured to further divide the first group into A1 to An subgroups;
    iv. computer readable program code configured to further divide the second group into B1 to Bn subgroups;
    v. computer readable program code configured to determine statistical individual variability between datasets selected from the plurality of three-dimensional image datasets in the A1 to An subgroups and the B1 to Bn subgroups;
    vi. computer readable program code configured to determine statistical individual variability between the plurality of three-dimensional image datasets in the first and second groups responsive to the statistical individual variability between datasets selected from the plurality of three-dimensional image datasets in the A1 to An subgroups and the B1 to Bn subgroups; and
    vii. computer readable program code configured to for each of the first and second groups, generate a reliability map comprising a map of probabilities that a voxel in an image dataset of the respective first and second groups satisfies a predetermined statistical threshold to thereby analyze brain images.

* * * * *